United States Patent
Sherwood et al.

(10) Patent No.: US 6,521,261 B2
(45) Date of Patent: *Feb. 18, 2003

(54) PHARMACEUTICAL EXCIPIENT HAVING IMPROVED COMPRESSIBILITY

(75) Inventors: Bob E. Sherwood, Amenia, NY (US); John H. Staniforth, Bath (GB); Edward A. Hunter, Glenham, NY (US)

(73) Assignee: Edward Mendell Co., Inc., Patterson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/981,319

(22) Filed: Oct. 16, 2001

(65) Prior Publication Data

US 2002/0142032 A1 Oct. 3, 2002

Related U.S. Application Data

(60) Continuation of application No. 09/754,760, filed on Jan. 4, 2001, now Pat. No. 6,358,533, which is a continuation of application No. 09/438,646, filed on Nov. 12, 1999, now Pat. No. 6,217,909, which is a continuation of application No. 08/992,073, filed on Dec. 17, 1997, now Pat. No. 6,103,219, which is a continuation of application No. 08/724,613, filed on Sep. 30, 1996, now Pat. No. 5,725,884, which is a division of application No. 08/370,576, filed on Jan. 9, 1995, now Pat. No. 5,585,115.

(51) Int. Cl.$^7$ ................................................. A61K 9/14
(52) U.S. Cl. ........................ 424/494; 424/400; 424/489; 424/495; 424/469; 424/470
(58) Field of Search ................................ 424/400, 489, 424/495, 469, 470

(56) References Cited

U.S. PATENT DOCUMENTS 6,217,909 B1 * 4/2001 Sherwood et al. ...... 23/313 AS
6,358,533 B2 * 3/2002 Sherwood et al. .......... 424/469

* cited by examiner

Primary Examiner—Thurman K. Page
Assistant Examiner—Charesse Evans
(74) Attorney, Agent, or Firm—Davidson, Davidson & Kappel, LLC

(57) ABSTRACT

A microcrystalline cellulose-based excipient having improved compressibility, whether utilized in direct compression, dry granulation or wet granulation formulations, is disclosed. The excipient is an agglomerate of microcrystalline cellulose particles and from about 0.1% to about 20% silicon dioxide particles, by weight of the microcrystalline cellulose, wherein the microcrystalline cellulose and silicon dioxide are in intimate association with each other. The silicon dioxide utilized in the novel excipient has a particle size from about 1 nanometer to about 100 microns. Most preferably, the silicon dioxide is a grade of colloidal silicon dioxide.

19 Claims, 5 Drawing Sheets

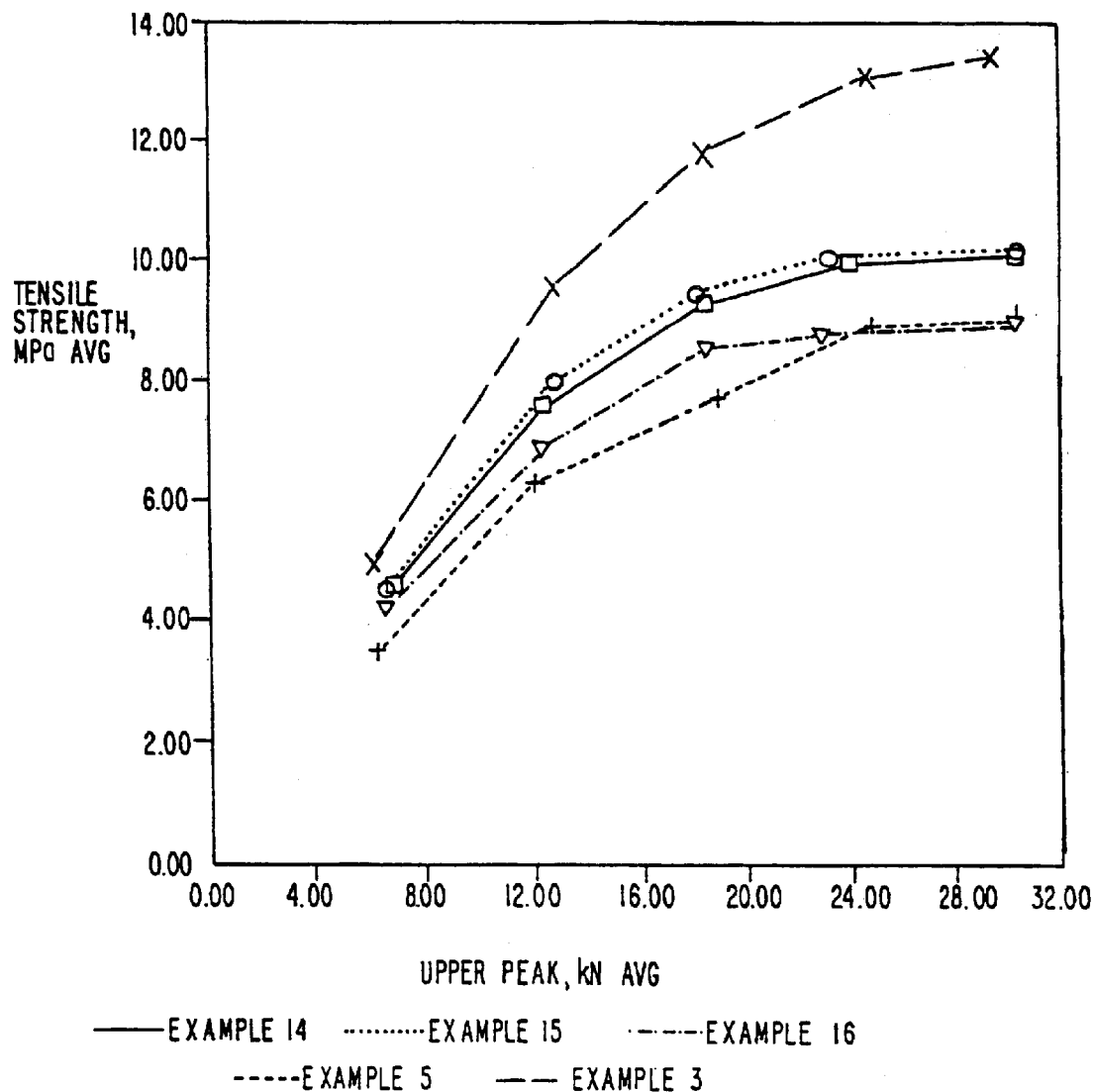

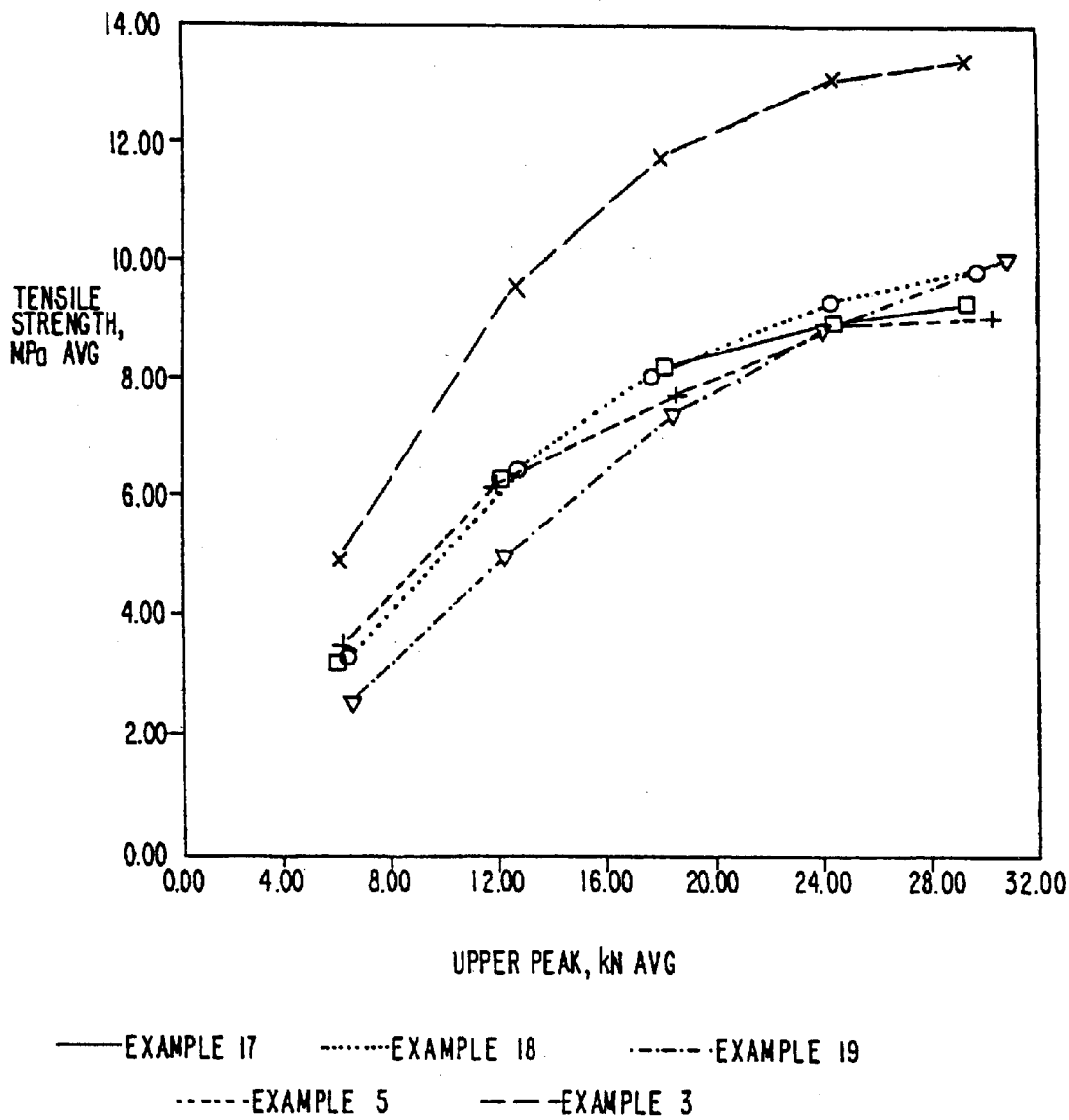

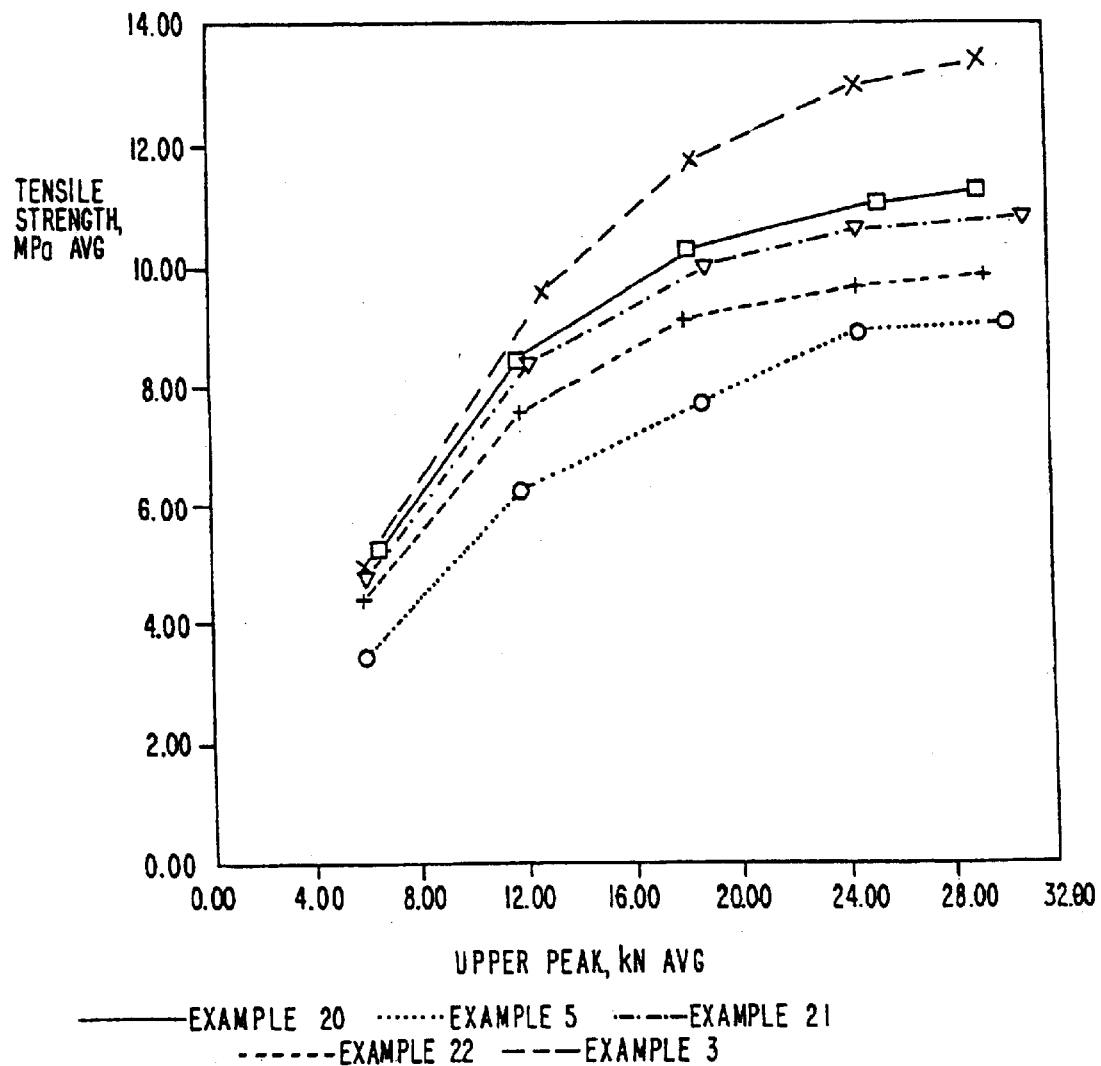

PHARMACEUTICAL EXCIPIENT HAVING IMPROVED COMPRESSIBILITY

This application is a continuation of U.S. patent application Ser. No. 09/754,760, filed Jan. 4, 2001 now U.S. Pat. No. 6,358,533; which is a continuation of U.S. patent application Ser. No. 09/438,646, filed Nov. 12, 1999 (now U.S. Pat. No. 6,217,909); which is a continuation of U.S. patent application Ser. No. 08/992,073, filed Dec. 17, 1997 (now U.S. Pat. No. 6,103,219); which is a continuation of U.S. patent application Ser. No. 08/724,613, filed Sep. 30, 1996 (now U.S. Pat. No. 5,725,884); which is a divisional of U.S. patent application Ser. No. 08/370,576, now Jan. 9, 1995 (now U.S. Pat. No. 5,585,115).

BACKGROUND OF THE INVENTION

The present invention relates to a novel excipient for use in the manufacture of pharmaceuticals, and in particular, solid dosage forms such as tablets which include one or more active ingredients.

In order to prepare a solid dosage form containing one or more active ingredients (such as drugs) it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to insure that the solid dosage form remains intact after compression.

In the case of tablets, the tablet is formed by pressure being applied to the material to be tabletted on a tablet press. A tablet press includes a lower punch which fits into a die from the bottom and a upper punch having a corresponding shape and dimension which enters the die cavity from the top after the tabletting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most drugs have none or only some of these properties, methods of tablet formulation have been developed in order to impart these desirable characteristics to the material(s) which is to be compressed into a solid dosage form. Typically, the material to be compressed into a solid dosage form Includes one or more excipients which impart the free-flowing, lubrication, and cohesive properties to the drug(s) which is being formulated into a dosage form.

Lubricants are typically added to avoid the material(s) being tabletted from sticking to the punches. Commonly used lubricants include magnesium stearate and calcium stearate. Such lubricants are commonly included in the final tabletted product in amounts of less than 1% by weight.

In addition to lubricants, solid dosage forms often contain diluents. Diluents are frequently added in order to increase the bulk weight of the material to be tabletted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethylcellulose.

There are three general methods of preparation of the materials to be included in the solid dosage form prior to compression: (1) dry granulation; (2) direct compression; and (3) wet granulation.

Dry granulation procedures may be utilized where one of the constituents, either the drug or the diluent, has sufficient cohesive properties to be tabletted. The method includes mixing the ingredients, slugging the ingredients, dry screening, lubricating and finally compressing the ingredients.

In direct compression, the powdered material(s) to be included in the solid dosage form is compressed directly without modifying the physical nature of the material itself.

The wet granulation procedure includes mixing the powders to be incorporated into the dosage form in, e.g., a twin shell blender or double-cone blender and thereafter adding solutions of a binding agent to the mixed powders to obtain a granulation. Thereafter, the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

The use of direct compression is limited to those situations where the drug or active ingredient has a requisite crystalline structure and physical characteristics required for formation of a pharmaceutically acceptable tablet. On the other hand, it is well known in the art to include one or more excipients which make the direct compression method applicable to drugs or active ingredients which do not possess the requisite physical properties. For solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed.

Typically, however, excipients are added to the formulation which impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

A processed cellulose, microcrystalline cellulose, has been utilized extensively in the pharmaceutical industry as a direct compression vehicle for solid dosage forms. Microcrystalline cellulose is commercially available under the tradename EMCOCEL®® from Edward Mendell Co., Inc. and as Avicel® from FMC Corp. Compared to other directly compressible excipients, microcrystalline cellulose is generally considered to exhibit superior compressibility and disintegration properties.

Another limitation of direct compression as a method of tablet manufacture is the size of the tablet. If the amount of active ingredient is high, a pharmaceutical formulator may choose to wet granulate the active with other excipients to attain an acceptably sized tablet with the desired compact strength. Usually the amount of filler/binder or excipients needed in wet granulation is less than that required for direct compression since the process of wet granulation contributes to some extent toward the desired physical properties of a tablet. Thus, despite the advantages of direct compression (such as reduced processing times and costs), wet granulation is widely used in the industry in the preparation of solid dosage forms. Many of those skilled in the art prefer wet granulation as compared to direct compression because this method has a greater probability of overcoming any problems associated with the physical characteristics of the various ingredients in the formulation, thereby providing a material which has the requisite flow and cohesive characteristics necessary to obtain an acceptable solid dosage form.

The popularity of the wet granulation process as compared to the direct compression process is based on at least three advantages. First, wet granulation provides the material to be compressed with better wetting properties, particularly in the case of hydrophobic drug substances. The addition of a hydrophilic excipient makes the surface of a hydrophobic drug more hydrophilic, easing disintegration and dissolution. Second, the content uniformity of the solid dosage forms is generally improved. Via the wet granulation method, all of the granules thereby obtained should contain approximately the same amount of drug. Thus, segregation of the different ingredients of the material to be compressed (due to different physical characteristics such as density) is avoided. Segregation is a potential problem with the direct compression method. Finally, the particle size and shape of the particles comprising the granulate to be compressed are optimized via the wet granulation process. This is due to the fact that when a dry solid is wet granulated, the binder "glues" particles together, so that they agglomerate in the granules which are more or less spherical.

Due to the popularity of microcrystalline cellulose, pharmaceutical formulators have deemed it desirable to include this excipient in a formulation which is wet granulated prior to tabletting. Unfortunately, currently-available microcrystalline cellulose does not hold to the typical principle that the amount of filler/binder needed in wet granulation is less than that in direct compression. It is known that the exposure of the microcrystalline cellulose to moisture in the wet granulation process severely reduces the compressibility of this excipient. The loss of compressibility of microcrystalline cellulose is particularly problematic where the formulation dictates that the final product will be relatively large in the environment of use. For example, if a pharmaceutical formulator desires to prepare a solid oral dosage form of a high dose drug, and the use of the wet granulation technique is deemed necessary, the loss of compressibility of the microcrystalline cellulose dictates that a larger amount of this material may be needed to obtain an acceptably compressed final product. The additional amount of microcrystalline cellulose needed adds cost to the preparation, but more importantly adds bulk, making the product more difficult to swallow.

The loss of compressibility of microcrystalline cellulose when exposed to wet granulation has long been considered a problem in the art for which there has been no satisfactory solution.

Attempts have been made to provide an excipient having high compressibility, a small bulk (high apparent density), and good flowability, while being capable of providing satisfactory factory disintegration of the solid dosage form, which is applicable to wet granulation as well as to dry granulation and direct compression methods for preparation of solid dosage forms.

For example, U.S. Pat. No. 4,159,345 (Takeo, et al.) describes an excipient which consists essentially of a microcrystalline cellulose having an average degree of polymerization of 60 to 375 and obtained through acid hydrolysis or alkaline, oxidative degradation of a cellulosic substance selected from linters, pulps and regenerated fibers. The microcrystalline cellulose is said to be a white cellulosic powder having an apparent specific volume of 1.6–3.1 cc/g, a repose angle of 35° to 42°, a 200-mesh sieve residue of 2 to 80% by weight and a tapping apparent specific volume of at least 1.4 cc/g.

In U.S. Pat. No. 4,744,987 (Mehra, et al.), a particulate co-processed microcrystalline cellulose and calcium carbonate composition is described wherein the respective components are present in a weight ratio of 75:25 to 35:65. The co-processed composition is said to be prepared by forming a well-dispersed aqueous slurry of microcrystalline cellulose and calcium carbonate and then drying the slurry to yield a particulate product. The combination of these two ingredients is said to provide a lower cost excipient which has tabletting characteristics similar to those of microcrystalline cellulose and which would satisfy a need for an economical excipient with good performance that is desired by the vitamin market.

European Patent Application EP 0609976A1 (assigned to Asahi Kasei Kabushiki Kaisha) describes an excipient comprising white powdery microcrystalline cellulose having an average degree of polymerization of from 100 to 375, preferably from 190 to 210, and an acetic acid holding capacity of 280% or more, preferably from 290 to 370%. The excipient is said to exhibit high compactability and a high rate of disintegration and is said to be obtained by heat-treating an aqueous dispersion of purified cellulose particles, which has a solids content of 40% or less by weight, at 100° C. or more, followed by drying, or by subjecting an aqueous dispersion of purified cellulose particles having a solids content of 23% or less by weight to thin film-forming treatment and drying the resultant thin film. The excipient is said to possess a high compressibility, and a good balance of compactability and rate of disintegration.

There still remains a need in the industry for a pharmaceutical excipient which possesses excellent compressibility whether utilized in a direct compression or wet granulation procedure.

OBJECTS AND SUMMARY OF THE INVENTION

It is an object of the present invention to provide an excipient which is useful in a variety of applications, and which may be utilized in direct compression or wet granulation methods.

It is a further object of the present invention to provide an excipient useful in direct compression methods which has improved compressibility relative to microcrystalline cellulose.

It is a further object of the present invention to provide an excipient useful in wet granulation methods which has improved compressibility relative to microcrystalline cellulose.

It is a further object of the present invention to provide a free-flowing excipient which has excellent compressibility properties when utilized in direct compression or wet granulation methods, and which furthermore possesses pharmaceutically acceptable disintegration properties.

It is a further object of the present invention to provide an improved microcrystalline cellulose excipient in which the microcrystalline cellulose has not been chemically altered, and which has improved compressibility relative to "off-the-shelf" commercially available microcrystalline cellulose.

It is a further object of the present invention to provide a solid dosage form which includes one or more active ingredients and the improved microcrystalline cellulose excipient of the present invention.

It is a further object of the present invention to provide an oral solid dosage form for one or more drugs which is economical to manufacture, which maintains its integrity during storage, and which possesses excellent disintegration and dissolution properties when exposed, e.g., to gastrointestinal fluid.

In accordance with the above objects and others which will be obvious to those skilled in the art, the present invention is directed to an excipient comprising a particulate agglomerate of coprocessed microcrystalline cellulose and from about 0.1% to about 20% silicon dioxide, by weight of the microcrystalline cellulose, the microcrystalline cellulose and silicon dioxide being in intimate association with each other, and the silicon dioxide portion of the agglomerate being derived from a silicon dioxide having a particle size from about 1 nanometer (nm) to about 100 microns ($\mu$m), based on average primary particle size.

In preferred embodiments, the silicon dioxide comprises from about 0.5% to about 10% of the excipient, and most preferably from about 1.25% to about 5% by weight relative to the microcrystalline cellulose.

In additional preferred embodiments of the invention, the silicon dioxide has a particle size from about 5 nm to about 40 $\mu$m, and most preferably from about 5 nm to about 50 $\mu$m.

In preferred embodiments of the present invention, the silicon dioxide is further characterized by a surface area from about 10 $m^2$g to about 500 $m^2/g$, preferably from about 50 $m^2/g$ to about 500 $m^2/g$, and more preferably from about 175 $m^2/g$ to about 350 $m^2/g$.

The present invention is further directed to an aqueous slurry useful in the preparation of a compressible excipient useful in dry and wet granulation formulation methods, comprising a mixture of microcrystalline cellulose and from about 0.1% to about 20% silicon dioxide, by weight relative to the microcrystalline cellulose, the silicon dioxide having a particle size from about 1 nm to about 100 $\mu$m. The solids content of the aqueous slurry is from about 0.5% to about 25%, by weight, preferably from about 15% to about 20% by weight, and most preferably from about 17% to about 19% by weight.

The present invention is further directed to a mixture of an active ingredient(s) and an excipient comprising a particulate agglomerate of coprocessed microcrystalline cellulose and from about 0.1% to about 20% silicon dioxide, by weight of the microcrystalline cellulose, the microcrystalline cellulose and silicon dioxide being in intimate association with each other, and the silicon dioxide having a particle size from about 1 nm to about 100 $\mu$m. The ratio of active ingredient to excipient is from about 1:99 to about 99:1, by weight.

The present invention is further directed to a granulate of an active ingredient(s) and the novel excipient described herein, wherein the active ingredient(s) and excipient have been subjected to a wet granulation procedure.

The present invention is further directed to a compressed solid dosage form comprising an active ingredient(s) and the novel excipient described herein, wherein the active ingredient(s) and excipient have been directly compressed into the solid dosage form or have been subjected to a wet granulation procedure and thereafter compressed into the solid dosage form. The compressed solid dosage form provides a suitable immediate release dissolution profile of the active ingredient(s) when exposed to aqueous solutions during in-vitro dissolution testing, and provides a release of drug in an environment of use which is considered bioavailable. In further embodiments of the invention, the dissolution profile of the solid dosage form is modified to provide a controlled or sustained release dissolution profile.

The present invention is further directed to a method of maintaining and/or enhancing the compressibility of microcrystalline cellulose. The method includes forming an aqueous slurry containing a mixture of microcrystalline cellulose and silicon dioxide having a particle size from about 1 nm to about 100 $\mu$m, and drying the slurry to obtain microcrystalline cellulose-based excipient particles in which the silicon dioxide particles have been integrated with the microcrystalline cellulose particles. Within this aspect of the invention, the slurry contains from about 0.5% to about 25% by weight microcrystalline cellulose, with amounts of from about 15% to about 20% being preferred. Furthermore, the slurry contains from about 0.25% to about 5% by weight silicon dioxide.

The novel excipient described herein is free-flowing, possesses excellent disintegration properties, and importantly, in certain embodiments possesses improved compressibility relative to normal "off-the-shelf" commercially available microcrystalline cellulose when directly compressed. The advantages of the novel excipient described herein are especially realized in pharmaceutical formulations prepared using wet granulation techniques. When utilized in wet granulation techniques, the novel excipient surprisingly provides a compressibility which is substantially improved in preferred embodiments in comparison to the compressibility of normal "off-the-shelf" commercially available microcrystalline cellulose used in wet granulation and is even comparable to "off-the-shelf" microcrystalline cellulose used in direct compression techniques. In other embodiments, the novel excipient surprisingly provides a compressibility which is substantially superior to the compressibility of normal "off-the-shelf" commercially available microcrystalline cellulose used in direct compression techniques.

The term "environmental fluid" is meant for purposes of the invention to encompass, e.g., an aqueous solution, or gastrointestinal fluid.

By "sustained release" it is meant for purposes of the invention that the therapeutically active medicament is released from the formulation at a controlled rate such that therapeutically beneficial blood levels (but below toxic levels) of the medicament are maintained over an extended period of time, e.g., providing a 12 hour or a 24 hour dosage form.

By "bioavailable" it is meant for purposes of the invention that the therapeutically active medicament is absorbed from the sustained release formulation and becomes available in the body at the intended site of drug action.

By "primary particle size" it is meant for purposes of the invention that the particles are not agglomerated. Agglomeration is common with respect to silicon dioxide particles, resulting in a comparatively average large agglomerated particle size.

BRIEF DESCRIPTION OF THE DRAWINGS

The following drawings are illustrative of embodiments of the invention and are not meant to limit the scope of the invention as encompassed by the claims.

FIG. 3 graphically shows a comparison of the tensile strength of tablets prepared in accordance with the invention to contain MCC coprocessed with diatomaceous earth, tablets containing MCC coprocessed with 2% w/w $SiO_2$ and prior art tablets prepared to contain only unmodified MCC.

FIG. 4 graphically illustrates a comparison of the tensile strength of tablets prepared using MCC coprocessed with silica gel, tablets prepared with the novel coprocessed MCC and tablets prepared with MCC alone.

FIG. 5 graphically illustrates a comparison of the tensile strength of tablets prepared using MCC coprocessed with HS 5 grade $SiO_2$, tablets prepared using coprocessed MCC-$SiO_2$ and prior art tablets prepared to contain only unmodified MCC.

DETAILED DESCRIPTION OF THE INVENTION

Figure 1:
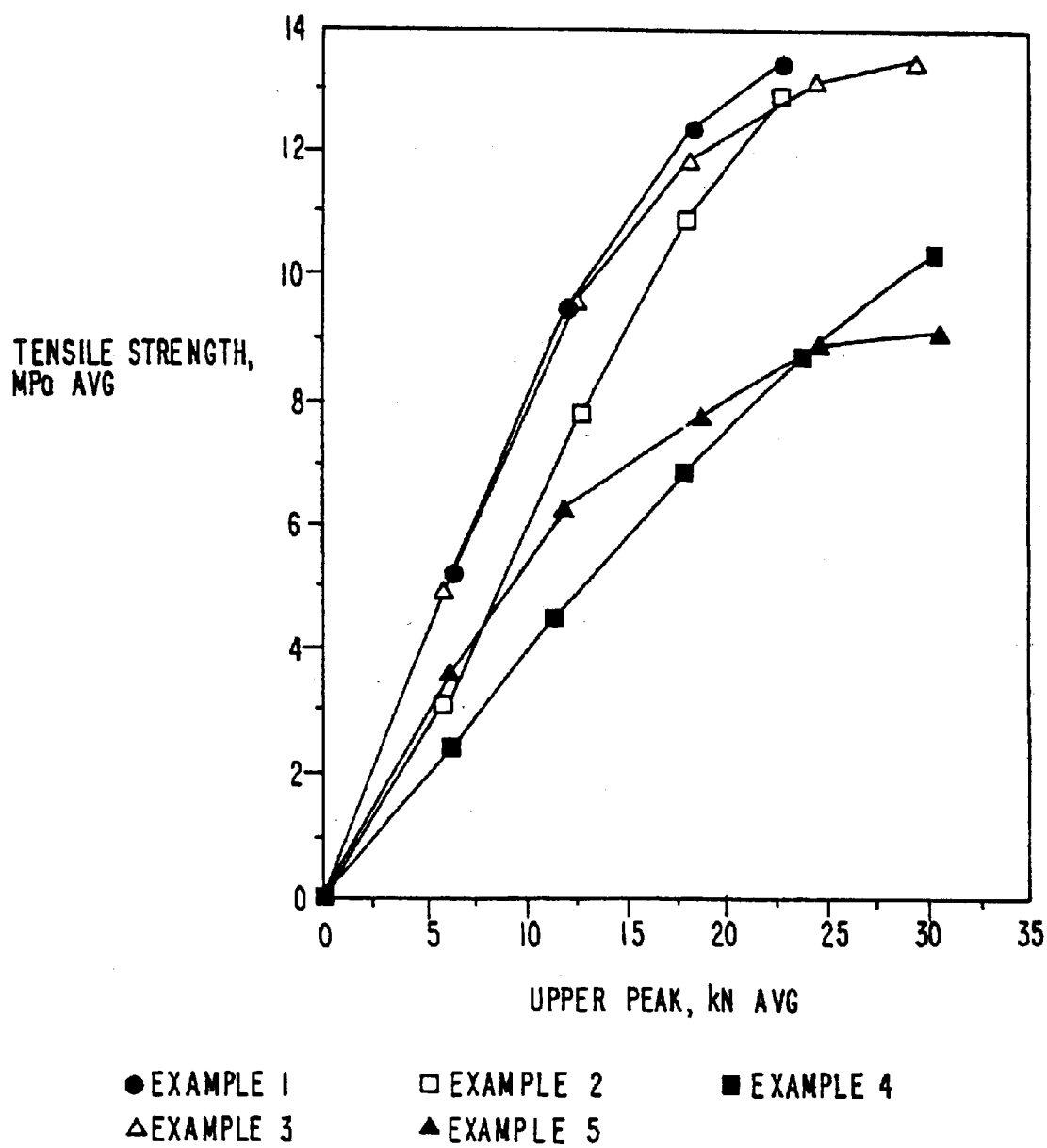
FIG. 1 graphically shows a comparison of the tensile strength of tablets prepared in accordance with the invention and prior art tablets.

Microcrystalline cellulose is a well-known tablet diluent and disintegrant. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and the aqueous slurry is spray dried to form dry, white odorless, tasteless crystalline powder of porous particles of a broad size distribution. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades which range in average particle size from 20 to 200 microns.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients.

Typically, microcrystalline cellulose has an apparent density of about 0.28 g/cm$^3$ and a tap density of about 0.43 g/cm$^3$. *Handbook of Pharmaceutical Excipients*, pages 53–55.

When utilized in pharmaceutical applications, microcrystalline cellulose is typically used as a tablet binder/diluent in wet granulation and direct compression formulations in amounts of 5–30% of the formulation, or more. However, it is known to use, more or less microcrystalline cellulose in pharmaceutical products, depending upon the requirements of the formulation.

Silicon dioxide is obtained by insolubilizing dissolved silica in sodium silicate solution. When obtained by the addition of sodium silicate to a mineral acid, the product is termed silica gel. When obtained by the destabilization of a solution of sodium silicate in such a manner as to yield very fine particles, the product is termed precipitated silica. Silicon dioxide is insoluble in water. Prior to the present invention, silicon dioxide, and in particular colloidal silicon dioxide, was used mainly as a glidant and anti-adherent in tabletting processes and encapsulation, promoting the flowability of the granulation. The amount of silicon dioxide included in such tablets for those applications is very limited, 0.1–0.5% by weight. *Handbook of Pharmaceutical Excipients*,©1986 American Pharmaceutical Association, page 255. This is due in part to the fact that increasing the amount of silicon dioxide in the mixture to be tabletted causes the mixture to flow too well, causing a phenomena known to those skilled in the tabletting art as "flooding". If the mixture flows too well, a varying tablet weight with uneven content uniformity can result.

Those skilled in the art will appreciate that the name and/or method of preparation of the silicon dioxide utilized in the present invention is not determinative of the usefulness of the product. Rather, as previously mentioned, it has been surprisingly discovered that it is the physical characteristics of the silicon dioxide which are critical. In particular, it has been discovered that silicon dioxide having a relatively large particle size (and correspondingly small surface area), such as silica gel, is not useful in the preparation of the improved microcrystalline cellulose products of the invention. The appended claims are deemed to encompass all forms of silicon dioxide having an average primary particle size from about 1 nm to about 100 $\mu$m, and/or a surface area from about 10 m$^2$/g to about 500 m$^2$/g.

The silicon dioxide utilized in the invention is of the very fine particle size variety. In the most preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E.I. DuPont & Co.; and W.R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred class of silicon dioxides utilized in the invention ranges from about 50 m$^2$/gm to about 500 m$^2$/gm. The average primary particle diameter of the preferred class of silicon dioxides utilized in the invention ranges from about 5 nm to about 50 nm. However, in commercial colloidal silicon dioxide products, these particles are agglomerated or aggregated to varying extents. The bulk density of the preferred class of silicon dioxides utilized in the invention ranges from about 20 g/l to about 100 g/l.

Commercially available colloidal silicon dioxide products have, for example, a BET surface area ranging from about 50±15 m$^2$/gm (Aerosil OX50) to about 400±20 (Cab-O-Sil S-17) or 390±40 m$^2$/gm (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0±8 g/l (Cab-O-Sil S-17) to 36.8 g/l (e.g., Cab-O-Sil M-5). The pH of the these products at 4% aqueous dispersion ranges from pH 3.5–4.5. These commercially available products are described for exemplification purposes of acceptable properties of the preferred class of silicon dioxides only, and this description is not meant to limit the scope of the invention in any manner whatsoever.

When the novel excipient of the invention utilizes a colloidal silicon dioxide, it has been found that the resultant excipient product surprisingly provides a compressibility which is substantially improved in preferred embodiments even in comparison to the compressibility of normal "off-the-shelf" commercially available microcrystalline cellulose used in direct compression techniques.

In other embodiments of the present invention, it has been discovered that the compressibility of microcrystalline cellulose which is wet granulated is significantly improved by a wider range of silicon dioxide products. Thus, in embodiments of the present invention where an improvement in overall compressibility of the microcrystalline cellulose (whether utilized in wet granulation or dry granulation) is not important, and the microcrystalline cellulose product is to be subjected to wet granulation, it has been discovered that the surface area of the silicon dioxide can be as low as about 50 $m^2$/gm and the average primary particle diameter can be as large as about 100 $\mu$m. Such silicon dioxide products are also deemed to be encompassed within the scope of the invention.

Both microcrystalline cellulose and silicon dioxide are substantially water insoluble. Therefore, the particle size of these ingredients as present in the well-dispersed aqueous slurry is directly related to the particle size of these two ingredients as they were introduced into the aqueous solution. There is no appreciable dissolution of either ingredient in the aqueous slurry.

After a uniform mixture of the ingredients is obtained in the suspension, the suspension is dried to provide a plurality of microcrystalline cellulose-based excipient particles having enhanced compressibility.

In the spray-drying process, the aqueous dispersion of microcrystalline cellulose and silicon dioxide is brought together with a sufficient volume of hot air to produce evaporation and drying of the liquid droplets. The highly dispersed slurry of microcrystalline cellulose and silicon dioxide is pumpable and capable of being atomized. It is sprayed into a current of warm filtered air, which supplies the heat for evaporation and conveys a dried product to a collecting device. The air is then exhausted with the removed moisture. The resultant spray-dried powder particles are approximately spherical in shape and are relatively uniform in size, thereby possessing excellent flowability. The coprocessed product consists of microcrystalline cellulose and silicon dioxide in intimate association with each other. Magnifications of the resultant particles indicate that the silicon dioxide is integrated with, or partially coats, the surfaces of the microcrystalline cellulose particles. When the amount of silicon dioxide including in the excipient is greater than about 20% by weight relative to the microcrystalline cellulose, the silicon dioxide appears to substantially coat the surfaces of the microcrystalline cellulose particles. The exact relationship of the two ingredients of the excipients after coprocessing is not presently understood; however, for purposes of description the coprocessed particles are described herein as including an agglomerate of microcrystalline cellulose and silicon dioxide in intimate association with each other. By "intimate association", it is meant that the silicon dioxide has in some manner been integrated with the microcrystalline cellulose particles, e.g., via a partial coating of the microcrystalline particles, as opposed to a chemical interaction of the two ingredients. The term "intimate association" is therefore deemed for purposes of the present description as being synonymous with "integrated" or "united". The coprocessed particles are not necessarily uniform or homogeneous. Rather, under magnification, e.g., scanning electron microscope at 500×, the silicon dioxide at the preferred percent inclusion appears to be an "edge-coating".

It is most preferred in the present invention that the microcrystalline cellulose and silicon dioxide are coprocessed, resulting in an intimate association of these ingredients, rather than being combined, e.g., as a dry mixture. In preferred embodiments of the present invention, the aqueous slurry of the microcrystalline cellulose and silicon dioxide are introduced into the spray dryer as a single aqueous medium. However, it is possible to separately introduce each ingredient into separate aqueous medium which are then combined. Other procedures for combining the microcrystalline cellulose and silicon dioxide known to those skilled in the art are deemed to be equivalent to the spray-drying technique described above, and are further deemed to be encompassed by the appended claims.

In certain preferred embodiments of the present invention, the coprocessing of the microcrystalline cellulose and silicon dioxide is accomplished by forming a well-dispersed aqueous slurry of microcrystalline cellulose and silicon dioxide, and thereafter drying the slurry and forming a plurality of microcrystalline cellulose-based excipient particles. Typically, microcrystalline cellulose is first added to an aqueous solution so that a slurry or suspension containing from about 0.5% to about 25% microcrystalline cellulose in the form of solids is obtained. Preferably, the slurry or suspension contains from about 15% to 20% microcrystalline cellulose and most preferably from about 17% to about 19% microcrystalline cellulose. At this stage, it is often desirable to adjust the pH of the slurry to about neutral with ammonium hydroxide, sodium hydroxide, and mixtures thereof or the like. The suspension is kept under constant agitation for a sufficient time to assure a uniform distribution of the solids prior to being combined with the silicon dioxide.

At this point, the silicon dioxide is added to the suspension or slurry in amounts ranging from 0.1% to about 20% by weight, based on the amount of microcrystalline cellulose, amounts from about 0.5% to about 10% are preferred while amounts of from about 1.25% to about 5% by weight are especially preferred. The silicon dioxide is preferably in colloidal form prior to addition to the MCC slurry. The microcrystalline cellulose and colloidal silicon dioxide are well-dispersed in the slurry or suspension prior drying and forming the novel particles.

It is preferred that the suspension be dried using spray-drying techniques, as they are known in the art. Other drying techniques, however, such as flash drying, ring drying, micron drying, tray drying, vacuum drying, radio-frequency drying, and possibly microwave drying, can also be used. The exact manner in which the suspension is dried is not believed to be critical for the microcrystalline cellulose/silicon dioxide particles to demonstrate enhanced compressibility after wet granulating.

Depending upon the amount and type of drying, the concentration of the microcrystalline cellulose and silicon dioxide in the suspension, the novel compressible particles will have different particle sizes, densities, pH, moisture content, etc.

The particulate coprocessed product of the present invention possesses desirable performance attributes that are not present when the combination of microcrystalline cellulose and silicon dioxide are combined as a dry mixture. It is believed that the beneficial result obtained by the combination of these two materials is due to the fact that the two materials are intimately associated with each other.

The average particle size of the integrated excipient of the present invention ranges from about 10 microns to about 1000 microns. Particle sizes of about 10–500 microns are preferred, particle sizes of about 30–250 microns are more preferred and particle sizes of about 40–200 microns are most preferred. It will be appreciated by those of ordinary skill in the art that the drying of the microcrystalline cellulosesilicon dioxide suspension results in a random size distribution of the novel excipient particles being produced. For example if spray drying techniques are used, droplet size, temperatures, agitation, dispersion, air flow, atomizer wheel speed, etc. will effect final particle size. Furthermore, it is within the scope of the invention to sort or mechanically alter the dried particles according to ranges of particle sizes depending upon end uses. The particle size of the integrated excipient is not narrowly critical, the important parameter being that the average size of the particle must permit the formation of a directly compressible excipient which forms pharmaceutically acceptable tablets.

The novel excipient has a bulk (loose) density ranging from about 0.2 g/ml to about 0.6 g/ml, and most preferably from about 0.35 g/ml to about 0.55 g/ml. The novel excipient has a tapped density ranging from about 0.2 g/ml to about 0.6 g/ml, and most preferably from about 0.35 g/ml to about 0.55 g/ml. The pH of the particles is most preferably about neutral, although granulates having a pH of from about 3.0 to about 8.5 are possible. The moisture content of the excipient particles will broadly range from about 0.5% to about 15%, preferably from about 2.5% to about 6%, and most preferably from about 3.0% to about 5% by weight.

The angle of repose is a measurement used to determine the flow characteristics of a powder. The angle of repose is subject to experiment and experimenter, but in a comparative test, the novel excipient is superior.

The novel excipient of the invention is free-flowing and directly compressible. Accordingly, the excipient may be mixed in the desired proportion with an active agent and optional lubricant (dry granulation), and then directly compressed into solid dosage forms. In preferred embodiments of the present invention wherein the silicon dioxide is colloidal silicon dioxide, the novel excipient comprising the coprocessed microcrystalline cellulose and colloidal silicon dioxide integrated together represents an augmented microcrystalline cellulose having improved compressibility as compared to standard commercially available grades of microcrystalline cellulose.

Alternatively, all or part of the excipient may be subjected to a wet granulation with the active ingredient. A representative wet granulation includes loading the novel excipient particles into a suitable granulator, such as those available from Baker-Perkins, and granulating the particles together with the active ingredient, preferably using an aqueous granulating liquid. The granulating liquid is added to the mixture with stirring until the powdery mass has the consistency of damp snow and then wet screened through a desired mesh screen, for example, having a mesh from about 12 to about 16. The screened granulate is then dried, using standard drying apparatus such as a convection oven before undergoing a final screening. Additional dry screening of this material is possible, such as by using screens of from about 40 to about 200 mesh. Those materials flowing through 40 and 60 mesh screens may be further ground prior to ultimate tablet formulation. The thus obtained wet granulate containing novel-excipient is now capable of undergoing tabletting or otherwise placed into a unit dosage form.

In certain preferred embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with conventional microcrystalline cellulose, or other excipients commonly used by those skilled in the art, depending of course upon the requirements of the particular formulation.

By virtue of the novel excipient of the present invention, the amount of the novel excipient compared to the amount of microcrystalline cellulose which must be used in a wet granulation technique to obtain an acceptable solid dosage form is substantially reduced.

In other embodiments of the invention, a further material is added to the slurry of microcrystalline cellulose and silicon dioxide. Such additional materials include non-silicon metal oxides, starches, starch derivatives, surfactants, polyalkylene oxides, cellulose ethers, celluloses esters and mixtures thereof. These additives may be included in desired amounts which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like.

An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5–3% by weight of the solid dosage form.

The complete mixture, in an amount sufficient to make a uniform batch of tablets, may then subjected to tabletting in a conventional production scale tabletting machine at normal compression pressures for that machine, e.g., about 1500–10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

In certain embodiments of the invention, the tablet is coated with a sufficient amount of a hydrophobic polymer to render the formulation capable of providing a release of the medicament such that a 12 or 24 hour formulation is obtained. The hydrophobic polymer which included in the tablet coating may be the same or different material as compared to the hydrophobic polymeric material which is optionally granulated with the sustained release excipient. In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100–555.

In further embodiments, the dosage form may be coated with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

The coatings which may be optionally applied to the compressed solid dosage form of the invention may comprise from about 0.5% to about 30% by weight of the final solid dosage form.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 μm if applied via spray-coating or immersion-coating. Generally, in embodiments of the invention wherein a hydrophobic polymer or enteric coating is applied to the tablets, the tablets are coated to a weight gain from about 1% to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g. from about 10% to about 40% of the total amount of medicament included in the formulation.

The active agent(s) which may be incorporated with the novel excipient described herein into solid dosage forms invention include systemically active therapeutic agents, locally active therapeutic agents, disinfecting agents, chemical impregnants, cleansing agents, deodorants, fragrances, dyes, animal repellents, insect repellents, a fertilizing agents, pesticides, herbicides, fungicides, and plant growth stimulants, and the like.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include anti-histamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the novel excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), anti-tussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), antiflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

Alternatively, the novel excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

DETAILED DESCRIPTION OF THE PREFERRED EMBODIMENTS

The following examples illustrate various aspects of the present invention. They are not to be construed to limit the claims in any manner whatsoever.

The examples set forth the preparation of various microcrystalline cellulose/silicon dioxide compositions. Tablets were prepared using each of the compositions and each of tablet preparations was tested for tensile strength.

EXAMPLES 1–3

PREPARATION OF COPROCESSED MCC-SiO$_2$ COMPOSITIONS AND GRANULATIONS THEREOF

EXAMPLE 1

MCC-SiO$_2$ Product-5% w/w SiO$_2$
A. Excipient Particles

In this example, about 6.2 kilograms of microcrystalline cellulose (MCC), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 5% w/w silicon dioxide (SiO$_2$), 200 m$^2$/g (CaboSil, PTG grade, available from Cabot Corp., Tuscola, Ill.) After allowing the materials to become intimately combined, the slurry was spray dried using a Niro Production Minor (Niro, Columbia, Md.), inlet temperature—215° C., outlet temperature—125° C., atomizer wheel speed 22,300 rpm, to provide MCC-SiO$_2$ having an average particle size of 40–60 microns.

B. Granulation of Excipient Particles

The MCC-SiO$_2$ particles obtained as a result of step 1A. were wet granulated in a Baker-Perkins 10 liter high-sheer granulator for 3 minutes using water as the granulating fluid. The resultant product was wet screened through a 12 mesh screen, tray dried in a convection oven for about 2–3 hours until a moisture content of less than 5% was obtained, dry screened and sieved to obtain an average particle size of from about 55 to about 70 microns.

EXAMPLE 2

MCC-SiO$_2$ Product-20% w/w SiO$_2$

The processes of Example 1A and B were repeated except that 20% w/w silicon dioxide was used to form the product.

EXAMPLE 3

MCC-SiO$_2$ Product-2% w/w SiO$_2$

In this example, the processes of Example 1A and B were repeated except that 2% w/w silicon dioxide was used to form the product.

EXAMPLE 4

Dry Blend Mix of MCC and SiO$_2$ (5% w/w)— Comparative

As a control, EMCOCEL® grade 50 M microcrystalline cellulose (Mendell Co., Inc.) and 5% w/w silicon dioxide, 200 m$^2$/g (CaboSil, PTG grade) were dry blended. No spray drying or other treatment of the mixture was undertaken. The method of Example 1B, however, was repeated.

EXAMPLE 5

Processed MCC without SiO$_2$

As a second control, the process described in Example 1B was repeated except that no SiO$_2$ was added.

EXAMPLE 6

In this example, batches of compressed tablets were prepared using each of the products obtained as a result of Examples 1–5. The tablets were prepared using a Korsch tablet press having a punch size of ⅜" and an aim weight of about 245 mg. The granulations were included in five separate tablettinig runs using compression forces of 6, 12, 18, 24 and 30 kN respectively. Ten tablets from each run were weighed, measured for diameter and tested for thickness and hardness on the Erweka TBH 30 tablet hardness tester to determine the compressibility of the microcrystalline cellulose as measured by tensile strength. The results of the analysis are graphically illustrated in FIG. 1 as a comparison of tensile strength versus compression force.

As can be seen from the graph, substantial benefits are obtained by coprocessing MCC with SiO$_2$. The tablets prepared using the products of comparative examples 4 and 5 demonstrated poor tensile strength. The novel excipient is superior and demonstrates approximately the same relative improvement across the entire range of compression forces. Furthermore, the graph also illustrates that tablets prepared with a mere dry admixture of MCC and SiO$_2$ (example 4 formulation) failed to demonstrate acceptable tensile strengths. Thus, the coprocessed MCC-SiO$_2$ described herein provides significant retention of MCC compressibility.

EXAMPLES 7–12

In these examples, compressed tablet products containing 70% by weight MCC and 30% acetaminophen (APAP herein) were prepared. The products of examples 7–9 were controls and prepared without the coprocessed MCC-SiO$_2$ of the present invention. The products of examples 10–12, on the other hand, included 70% by weight of the novel coprocessed MCC-SiO$_2$ and 30% APAP. Details concerning the preparation of each granulation product is set forth below. A graphical comparison of the tensile strength versus compression force for each tabletted product is provided in FIG. 2.

EXAMPLE 7

Intragranulation and Extragranulation of APAP with MCC

In this example, tablets were prepared using off-the-shelf MCC (EMCOCEL® 50 M) according to the following formula:

| INGREDIENTS | WEIGHT (GRAMS) |
|---|---|
| MCC | 267.9 |
| APAP | 114.8 |
| Deionized water | 165.8 |

One half of the MCC was added to a Baker-Perkins 10 liter blender and combined with all of the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and dried in a convection oven for 2–3 hours at 60° C. until a moisture content of less than 5% was obtained. The granulation was then dry screened through a 16 mesh screen before being blended for 10 minutes with the remaining portion of the MCC in a 2 quart V-blender. The granulation was removed from the blender and tabletted in accordance with the method described below.

TABLET STRENGTH TESTING

In order to prepare tablets for the formulations of examples 7, 8, 10 and 11, the following procedure was used:
the wet granulation products were weighed and mixed in a 2 quart V-blender for 5 minutes with 0.2% Pruv™ (sodium stearyl fumarate, available from Mendell Co., Inc.).

Five separate tabletting runs were undertaken with compression forces of 5, 10, 15, 20 and 25 kN respectively using a Korsch tablet press having a punch size of ⅜" and an aim weight of about 245 mg. Ten tablets from each compression force were selected and used in the experiment set forth in Example 13.

EXAMPLE 8

Wet Granulation of APAP with MCC

In this example, only wet granulation or the intragranulation step as described above was undertaken. The formulation was prepared according to the following formula using off-the-shelf EMCOCEL® 50 M MCC:

| INGREDIENTS | WEIGHT (GRAMS) |
|---|---|
| MCC | 178.6 |
| APAP | 76.5 |
| Deionized water | 170.1 |

The MCC was added to a Baker-Perkins 10 liter blender and combined with the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven at 60° C. for 2–3 hours, until a moisture content of less than 5% was achieved. The granulation was then dry screened through a 16 mesh screen and tabletted in accordance with the method described in example 7.

EXAMPLE 9

Direct Compression Formulation of APAP with MCC

A direct compression formulation for tablets was prepared to contain 70% off-the-shelf EMCOCEL® 50 M MCC and 30% APAP by weight. The tablets were prepared according to the following formula:

| INGREDIENTS | WEIGHT (GRAMS) |
|---|---|
| MCC | 175.0 |
| APAP | 74.5 |
| PRUV | 0.5 |

The MCC and APAP were combined in a V-blender and mixed for 15 minutes. Thereafter, the Pruv was added and mixing was continued for another 5 minutes. The granulation was removed and five separate tabletting runs were undertaken using compression forces of 5, 10, 15, 20 and 25 kN respectively on a Korsch tablet press. The tablet press had a punch size of ⅜" and an aim weight of about 245 mg. Ten tablets from each compression force were used in the experiment set forth in Example 13.

EXAMPLE 10

Wet Granulation of APAP with Coprocessed MCC-SiO$_2$ (5% w/w)

In this example, tablets were prepared by wet granulation with the coprocessed MCC (5% w/w SiO$_2$) of Example 1A. The tablet granulation was prepared according to the following formula:

| INGREDIENTS | WEIGHT (GRAMS) |
|---|---|
| MCC-SiO$_2$ | 178.6 |
| APAP | 76.5 |
| Deionized water | 170.1 |

The MCC-SiO$_2$ was added to a Baker-Perkins 10 liter blender and combined with the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven for 2–3 hours at 60° C. until a moisture content of less than 5% was achieved. The granulation was then dry screened through a 16 mesh screen and tabletted according to the method set forth in Example 7.

EXAMPLE 11

Intra- and Extragranulation of APAP with MCC-SiO$_2$ (5% w/w)

A granulation for compressed tablets was prepared according to the following formula:

| INGREDIENTS | WEIGHT (GRAMS) |
|---|---|
| MCC-SiO$_2$ | 267.9 |
| APAP | 114.8 |
| Deionized water | 165.8 |

One half of the coprocessed MCC-SiO$_2$ (prepared as in Example 1A) was added to a Baker-Perkins 10 liter blender and combined with all of the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven for 2–3 hours at 60° C. until a moisture content of less than 5% was achieved. The granulation was then dry screened through a 16 mesh screen before being blended for 10 minutes with the remaining portion of the coprocessed MCC-SiO$_2$ in a 2 quart V-blender, removed from the blender, and tabletted according to the method of Example 7.

EXAMPLE 12

Direct Compression Formulation of APAP with MCC-SiO$_2$ (5% w/w)

A direct compression formulation similar to that set forth in example 9 was undertaken except that the tablets were prepared to contain the coprocessed MCC-SiO$_2$ of Example 1A. The tablet granulation was prepared according to the following Formula:

| INGREDIENTS | WEIGHT (GRAMS) |
|---|---|
| MCC-SiO$_2$ | 175.0 |
| APAP | 74.5 |
| PRUV | 0.5 |

As was the case in example 9, five separate tabletting runs were undertaken using compression forces of 5, 10, 15, 20 and 25 kN respectively on a Korsch tablet press, (punch size: ⅜" and aim weight—about 245 mg). Ten tablets from each compression force were used to carry out the experiment set forth in Example 13.

EXAMPLE 13

TABLET STRENGTH TESTING

Ten tablets from each compression force run for each formulation prepared in Examples 7–12 were weighed, measured for diameter and tested for thickness and hardness on the Erweka TBH 30 tablet hardness tester to determine the compresibility of the microcrystalline cellulose. The results are graphically illustrated in FIG. 2 as a comparison tensile strength versus compression force.

Figure 2:
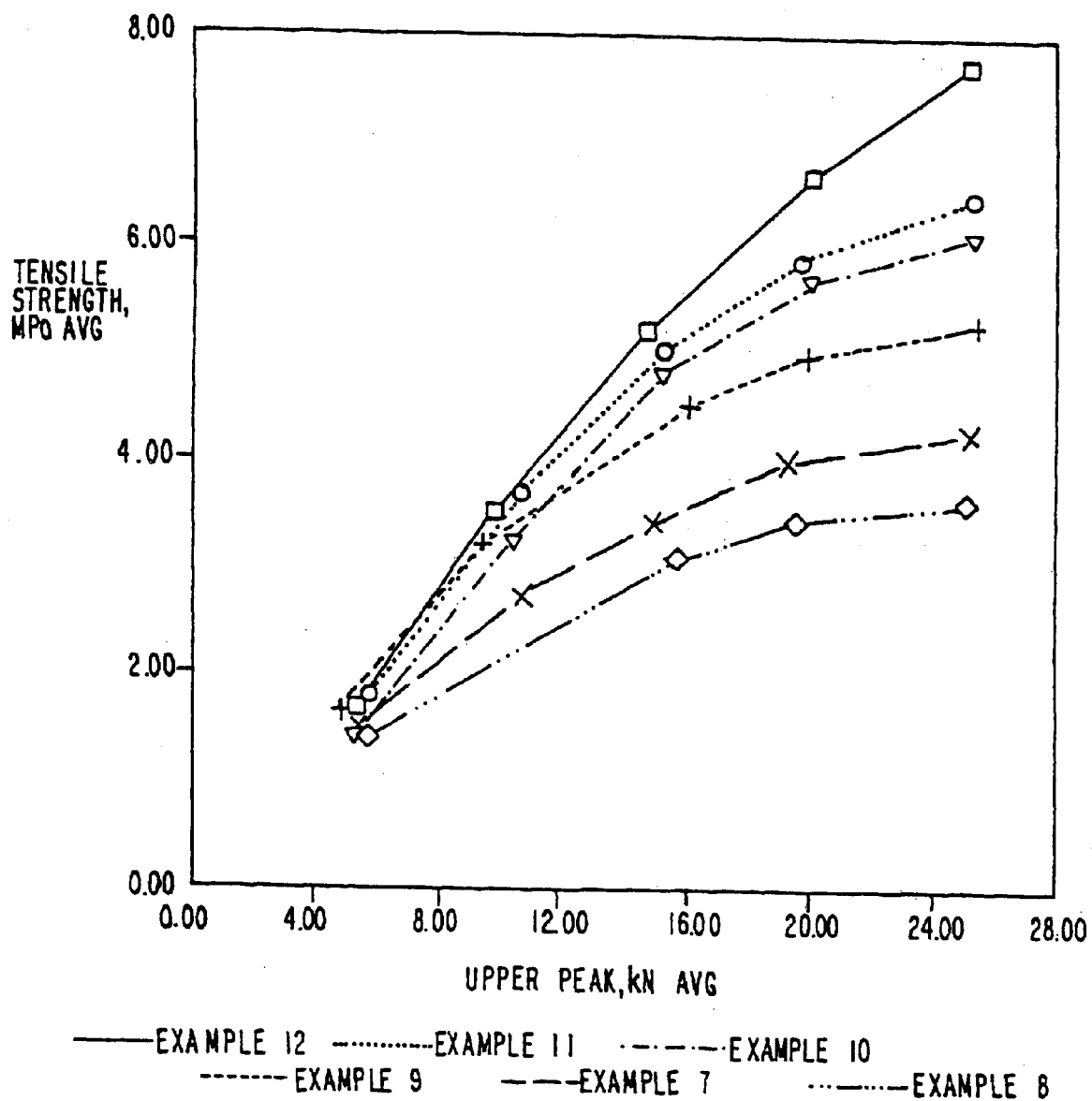
FIG. 2 graphically shows a comparison of the tensile strength of APAP containing tablets prepared in accordance with the invention and prior art APAP containing tablets.

Referring now to FIG. 2, it can be seen that compressed tablets made with the inventive coprocessed MCC-SiO$_2$ have relatively high tensile strengths when compared to those made with off-the-shelf MCC. The advantages of the coprocessed MCC-SiO$_2$ are clearly seen in both direct compression and wet granulation formulations and especially in wet granulation products.

EXAMPLES 14–16

DIATOMACEOUS EARTH

In these examples, the coprocessing method described in Example 1A was repeated except that diatomaceous earth of about 40 micron particle size (J. T. Baker, Phillipsburg, N.J. was the source of SiO$_2$).

| Example | Diatomaceous Earth (wt %) |
|---|---|
| 14 | 2.0 |
| 15 | 1.0 |
| 16 | 0.5 |

The resultant granulates prepared according to Example 1B were tabletted according to the same method described in Example 6 and evaluated for tensile strength. The products of intentive Example 3 (MCC-SiO$_2$ 2% w/w) and Example 5 (MCC alone) were included in FIG. 3 for comparison purposes.

Referring now to FIG. 3, it can be seen that although the retention of compressibility afforded by coprocessing diatomaceous earth is not as great as that provided by colloidal SiO$_2$ having surface areas of about 200 m$^2$/g, the co-processed MCC-diatomaceous earth nonetheless demonstrates improved compressibility in wet granulation formulations.

EXAMPLES 17–19

SILICA GEL

In these examples, the coprocessing method described in Example 1A was repeated using silica gel 200 micron particle size (VWR Corp., Piscataway, N.J. as the source of $SiO_2$).

| Example | Silica Gel (wt %) |
|---------|-------------------|
| 17 | 1 |
| 18 | 2 |
| 19 | 5 |

The resultant granulates prepared according to Example 1B were tabletted according to the same method described in Example 6 and evaluated for tensile strength. The products of inventive Example 3 (MCC-$SiO_2$ 2% w/w) and Example 5 (MCC alone) were included in FIG. 4 for comparison purposes.

Referring now to FIG. 4, it can be seen that the retention of compressibility afforded by coprocessing with silica gel is well below that provided by colloidal $SiO_2$ having surface areas of about 200 $m^2/g$. In fact, MCC co-processed with silica gel demonstrates compressibility properties about the same as off-the-shelf MCC in wet granulation formulations.

EXAMPLES 20–22

HS-5 Trade Silicon Dioxide

In these examples, the coprocessing method described in example 1 was repeated using HS-5 grade $SiO_2$ surface area—325 $m^2/g$ (Cabot Corp., Tuscola, Ill.).

| Example | Silica Gel (wt %) |
|---------|-------------------|
| 20 | 2 |
| 21 | 1 |
| 22 | 0.5 |

The resultant granulates prepared according to Example 1B were tabletted according to the same method described in Example 6 evaluated for tensile strength. The products of inventive Example 3 (MCC-$SiO_2$ 2% w/w) and Example 5 (off-the-shelf MCC) were included in FIG. 5 for comparison purposes.

Referring now to FIG. 5, the retention of compressibility afforded by coprocessing with HS-5 is comparable to that obtained using $SiO_2$ having surface areas of about 200 $m^2/g$.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A pharmaceutical composition comprising:
   an excipient including microcrystalline cellulose in intimate association with 0.1% to 20% w/w silicon dioxide; and
   an active agent, wherein the pharmaceutical composition is formed by mixing the excipient, the active agent, and water to form a mixture, and then drying the mixture to obtain the pharmaceutical composition.

2. A method for preparing a pharmaceutical composition, comprising:
   mixing an excipient, an active agent, and water to obtain a mixture; and
   drying the mixture to obtain the pharmaceutical composition, wherein the excipient includes microcrystalline cellulose in intimate association with 0.1% to 20% w/w silicon dioxide.

3. A tablet comprising:
   an excipient including microcrystalline cellulose in intimate association with 0.1% to 20% w/w $SiO_2$; and
   an active agent, wherein the tablet is formed by mixing the excipient, the active agent, and water to form a mixture, and then drying and tabletting the mixture.

4. The pharmaceutical composition of claim 1, wherein said silicon dioxide has an average primary particle size from about 1 nm to about 100 $\mu$m, and said excipient has a bulk density of from about 0.35 g/ml to about 0.6 g/ml.

5. The pharmaceutical composition of claim 4, wherein said silicon dioxide has an average primary particle size from about 5 nm to about 40 $\mu$m.

6. The pharmaceutical composition of claim 4, wherein said silicon dioxide is derived from colloidal silicon dioxide.

7. The pharmaceutical composition of claim 4, wherein said silicon dioxide is included in an amount of from about 0.5% to about 10% by weight, based on the weight of said microcrystalline cellulose.

8. The pharmaceutical composition of claim 4, wherein said silicon dioxide is included in an amount of from about 1.25% to about 5% by weight, based on the weight of said microcrystalline cellulose.

9. The pharmaceutical composition of claim 4, wherein said excipient particles have an average particle size of from about 10 $\mu$m to about 1,000 $\mu$m.

10. The pharmaceutical composition of claim 4, wherein said excipient particles have an average particle size of from about 10 $\mu$m to about 500 $\mu$m.

11. The pharmaceutical composition of claim 4, wherein said excipient particles have an average particle size of from about 30 $\mu$m to about 250 $\mu$m.

12. The pharmaceutical composition of claim 4, wherein said excipient particles have a moisture content from about 0.5% to about 15%.

13. The pharmaceutical composition of claim 4, wherein said excipient particles further comprise a member of the group consisting of non-silicon metal oxides, starches, starch derivatives, surfactants, polyalkylene oxides, celluloses, cellulose ethers, cellulose esters and mixtures thereof.

14. The pharmaceutical composition of claim 4, wherein said silicon dioxide is derived from a silicon dioxide having a surface area from about 10 $m^2/g$ to about 500 $m^2/g$.

15. The pharmaceutical composition of claim 4, wherein said silicon dioxide is derived from a silicon dioxide having a surface area from about 175 $m^2/g$ to about 350 $m^2/g$.

16. The pharmaceutical composition of claim 4, wherein said excipient has a bulk density from about 0.35 g/ml to about 0.55 g/ml.

17. The pharmaceutical composition of claim 9, wherein said silicon dioxide is derived from a silicon dioxide having an average primary particle size from about 5 nm to about 40 $\mu$m.

18. The pharmaceutical composition of claim 9, wherein said silicon dioxide is derived from colloidal silicon dioxide.

19. The pharmaceutical composition of claim 1, wherein said silicon dioxide is integrated with or partially coats said microcrystalline cellulose.

* * * * *